(12) United States Patent
Tsimerman et al.

(10) Patent No.: US 6,991,356 B2
(45) Date of Patent: Jan. 31, 2006

(54) LED CURING LIGHT

(76) Inventors: Efraim Tsimerman, Suite 903 West, 480 Queens Quay West, Toronto, Ontario (CA), M5V 2Y5; Emil Chouster, Apt. 410, 360 Ridelle Avenue, Toronto, Ontario (CA), M6B 1K1

( * ) Notice: Subject to any disclaimer, the term of this patent is extended or adjusted under 35 U.S.C. 154(b) by 125 days.

(21) Appl. No.: 10/323,894

(22) Filed: Dec. 20, 2002

(65) Prior Publication Data

US 2004/0120162 A1 Jun. 24, 2004

(51) Int. Cl.
*A61C 1/00* (2006.01)

(52) U.S. Cl. ........................ 362/573; 362/800; 362/804; 313/501; 313/506

(58) Field of Classification Search ................. 362/800, 362/804, 119; 313/110, 501, 506
See application file for complete search history.

(56) References Cited

U.S. PATENT DOCUMENTS 6,102,696 A    8/2000  Osterwalder et al.
6,103,203 A    8/2000  Fischer
6,331,111 B1 * 12/2001  Cao ............................. 433/29

FOREIGN PATENT DOCUMENTS

| DE | 100 40 875 A 1 | 3/2002 |
| WO | WO 99/35995 | 2/1999 |
| WO | WO 99/16136 | 4/1999 |
| WO | WO 00/13608 | 3/2000 |
| WO | WO 02/11640 A2 * | 8/2001 |
| WO | WO 02/11640 A2 | 2/2002 |

* cited by examiner

*Primary Examiner*—Sandra O'Shea
*Assistant Examiner*—Anabel Ton
(74) *Attorney, Agent, or Firm*—Bereskin & Parr (57) ABSTRACT

A light source which may be used as part of a dental curing lamp is comprised of at least one, and preferably a plurality, of LEDs. To increase the efficiency of the light output the LEDs are encapsulated in a beam converger including an extractor portion and a collimator portion. Light rays leaving the collimator portion have an angle which matches the entrance angle input requirements of an associated light guide. In another aspect, cooling of LEDs is accomplished by reservoirs located in a hand piece and in a base station. In another aspect of the invention, cooling is achieved by use of a heat pipe and a cooling jacket. The cooling jacket may contain a material having a high latent heat of fusion at a phase change temperature suitable for cooling the LEDs.

47 Claims, 10 Drawing Sheets

LED CURING LIGHT

FIELD OF THE INVENTION

This invention relates to the field of curing lights and in particular curing lights as used in the field of health care, particularly, within dentistry.

BACKGROUND OF THE INVENTION

Curing lights are devices which are used to create a beam of light of an appropriate wavelength to cause curing of photosensitive materials. Various sources of light have been used within curing lights. The source of light may be a halogen bulb, a Xenon bulb, and more recently light emitting devices herein referred to as LEDs.

One of the advantages of using LEDs as the light source arises from the fact that the emission spectrum of some LEDs, in particular, blue LEDs, is in a very narrow band which coincides with the peak of the absorption spectrum of camphorquinone, the most common photoactivator in dental photosensitive materials. Because of the narrow band, almost all of the light energy reaching the material is useful in the process of activating polymerization. No unnecessary heat is applied to the tooth. One of the problems with LED curing lights however is that their light output intensity is relatively low. Because of the low output, LED curing lights are at a disadvantage in the speed of cure as compared with more intense light sources such as halogen bulbs, plasma arc or xenon light sources.

With recent advances in LED technology, there are now available on the market more higher powered individual encapsulated LEDs. One example is the LED sold under the trade mark LUXEON from LUMILEDS™ Lighting LLC. This product can produce up to 500 mW of light output. One of the problems of these types of LEDs is that their light beam is highly divergent, often as much as 160°. This in turn means that much of the light, perhaps as much as 70% will be lost if the LED is coupled directly to a fibreoptic light guide with a typical numerical aperture of 0.5. Numerical aperture is the sine of the acceptance half angle for a particular light guide. A 0.5 numerical aperture means that all rays with a divergence of greater than 30° will not be accepted into the light guide and therefore will be ineffective. If it is desired to compensate for these loses by using a large number of these types of LEDs, their large size, typically 8 mm in diameter, precludes one from doing so since a typical dental light guide has a diameter of not greater than 13 mm with the average being more typically 9 to 10 mm. On the other hand, if used without a light guide, that is, directly at the surface contacting the tooth, it is still not possible to productively use more than one LED of this type because the dimensions of the typical tooth involved would still not be greater than 11×10 mm. Theoretically it is possible to use unencapsulated LEDs, more particularly referred to as dies and pack them more closely in an assembly. However in this case, the light beam becomes even more divergent, typically about 180° and the heat generated from a high number of such dies within the device may create difficulty with respect to cooling. Most existing LED curing lights do not provide a light output intensity of greater than 500 mW/cm² whereas curing lights using more typical light sources can reach outputs of 2,500 mW/cm².

Accordingly, there exists a need for a structure which would permit utilization of LEDs as are commercially available, but which are capable of producing the desired light output.

SUMMARY OF THE INVENTION

In accordance with this invention, a light source for a curing light comprises at least one LED die. The light source includes electrical connection means for conducting electrical current to energize the LED die. The LED die is arranged with its light emitting face arranged to emit light in the forward direction relative to the LED die. The light source further includes a beam converger which is adjacent to the light emitting face. The beam converger includes an extractor portion. The extractor portion has a truncated, generally conical shape which tapers outwardly and forwardly relative to the LED die.

In a particularly preferred embodiment of the invention, the light source comprises a plurality of LED dies and the LED dies are arranged in an array with the light emitting faces arranged to emit light in the forward direction.

In accordance with another aspect of the invention, the beam converger further includes a collimator portion. The collimator portion may be solid. Alternatively, the collimator portion may be hollow and in this case has a mirrored internal surface for reflecting light.

In accordance with a further preferred embodiment of the invention, the invention includes a light source having a plurality of LED dies as referred to above in combination with a light guide wherein the maximum angle of light rays exiting from the beam converger is equal to or less than the acceptance angle of the light guide.

In accordance with another aspect of the invention, the light source as explained above, includes a source of cooling fluid and circulation means for circulating the cooling fluid through a heat sink for conducting heat away from an array of LED dies. In a particularly preferred embodiment, the source of cooling fluid includes a first cooling fluid reservoir, a first pump for circulating fluid from the first reservoir to the heat sink and a second reservoir and pump means to circulate cooling fluid from the second reservoir to and from the first reservoir.

In accordance with another aspect of the invention, the curing light may be a combination of a base station and a hand held unit interconnected by a supply conduit. Alternatively, the curing light may include a base station and a hand held unit which is not connected by a supply conduit, with the two components being interconnectable when the hand held unit is parked in the base station to provide circulation of cooling fluid and recharging of a battery as necessary.

BRIEF DESCRIPTION OF THE DRAWINGS

Details of the invention and various embodiments thereof will be further understood with reference to the drawings set out below, and wherein:

FIG. 14c is an elevational view of the assembly of FIG. 14a;

DETAILED DESCRIPTION OF THE INVENTION

In order to more clearly understand the effect of the light output of LEDs, or a matrix of LEDs, it is first useful to consider the output.

Figure 1:
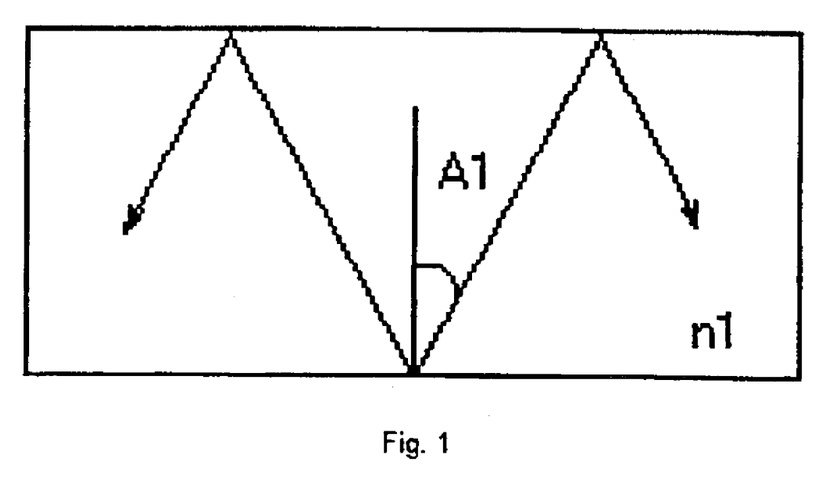
FIG. 1 is a cross-section showing light ray patterns in a block of material having an index of refraction of $n_1$.

For the sake of simplicity, the following discussion assumes that the LED light output is a hemispherical shape. The following figures illustrate sections through a cone showing the angles of the rays of emitted light. Accordingly, FIG. 1 indicates that from the total amount of light, originated within an LED, only the portion within the spherical angle of +/− A1 as shown in FIG. 1 can escape into the ambient air through the light emitting surface (hereinafter referred to as the forward facing surface) of the die. The value of the angle A1 is given by the equation:

$$\sin(A1) = \frac{1}{n_1} \quad (1)$$

where $n_1$ is the index of refraction of the material of the LED die.

The efficiency of light extraction is given by the equation:

$$Ef = 1 - \cos(A1) \quad (2)$$

Figure 2:
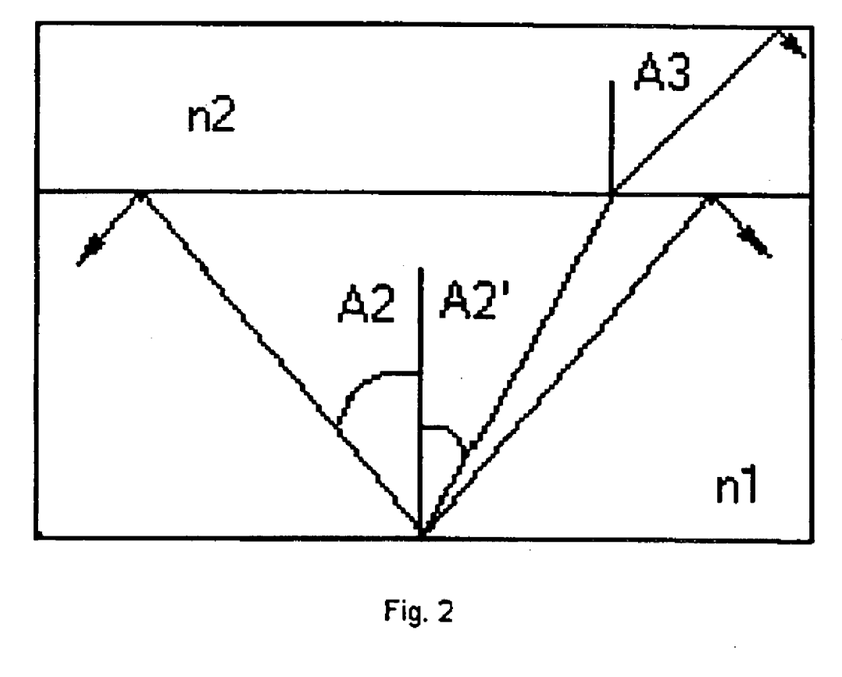
FIG. 2 is a view similar to FIG. 1 but shows light ray patterns in a block of material having a first section of index of refraction $n_1$ and a second portion having an index of refraction $n_2$.

In the case of blue LEDs, $n_1=2.4$. A1 is about 25° and the Ef=9.4%. If the ray from the die escapes into a material different than air, and that material has a refraction index of $n_2$ as shown in FIG. 2, then equation 1 changes to:

$$\sin(A2) = \frac{n_2}{n_1} \quad (3)$$

For polymethyalmethacrylate for example, $n_2=1.5$. Then A2 is about 39° and Ef=22.3%. This shows that this is more than double the amount for a bare die. However, at the interface between the polymethyalmethacrylate and air, there is another efficiency drop due to the fact that only rays which are within the ±/−A3 angle in the polymethyalmethacrylate can escape into air. In this case:

$$\sin(A3) = \frac{1}{n_2} \quad (4)$$

The value of the edge ray A2' (the edge ray is the most divergent ray originated in the die, which can escape into air) is given by the equation:

$$\sin(A2') = \frac{1}{n_2} \times \frac{n_2}{n_1} = \frac{1}{n_1}$$

which means that A2'=A1 and therefore the efficiency of such a "sandwich" structure is only equal to that of the bare die.

This analysis indicates that the way to increase the total extraction efficiency is to have all rays entering the intermediate layer having a refraction index of $n_2$ strike the exit aperture at an angle with a value less than the critical, that is:

$$\sin(\phi) < \frac{1}{n_2}$$

This assures the ray transition through the intermediate layer to air boundary.

In accordance with this invention, there is a device which can dramatically increase efficiency. In this disclosure the device is referred to as a beam converger. The beam converger 20 includes a reverse taper extractor portion 22 and optionally, a collimator portion 24 (see FIGS. 3–8).

Figure 3:
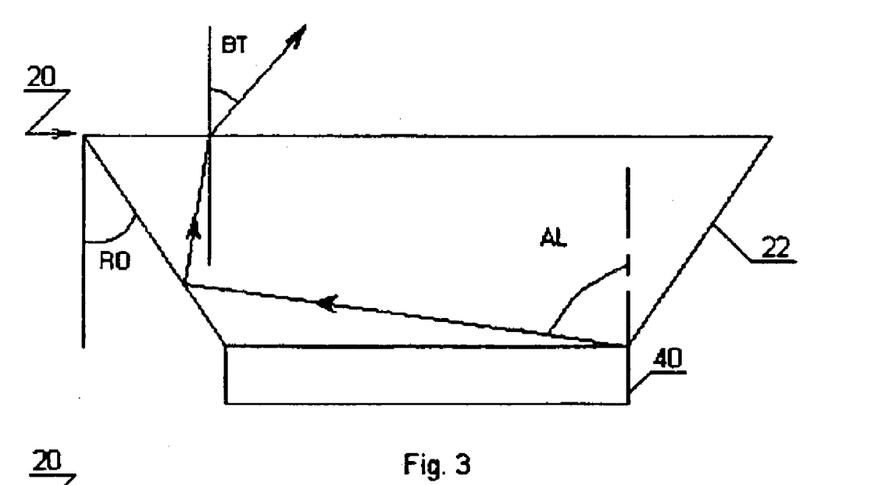
FIG. 3 is a cross-sectional diagram showing light ray patterns in a beam converger in accordance with a first embodiment of the invention.
Figure 4:
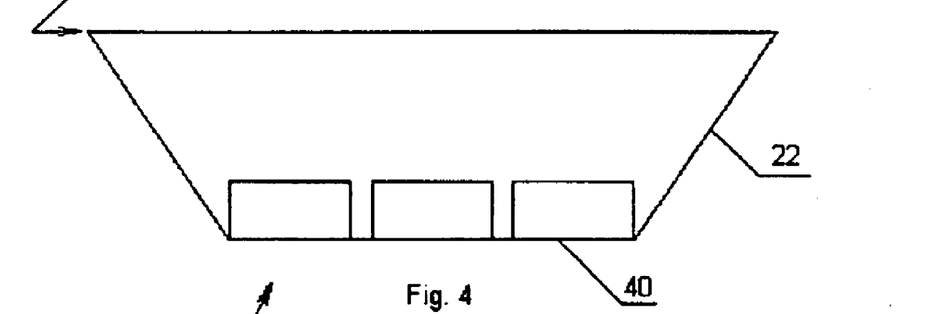
FIG. 4 is a view similar to FIG. 3 showing further light ray patterns and geometric relationships of a beam converger in accordance with the invention.
Figure 5:
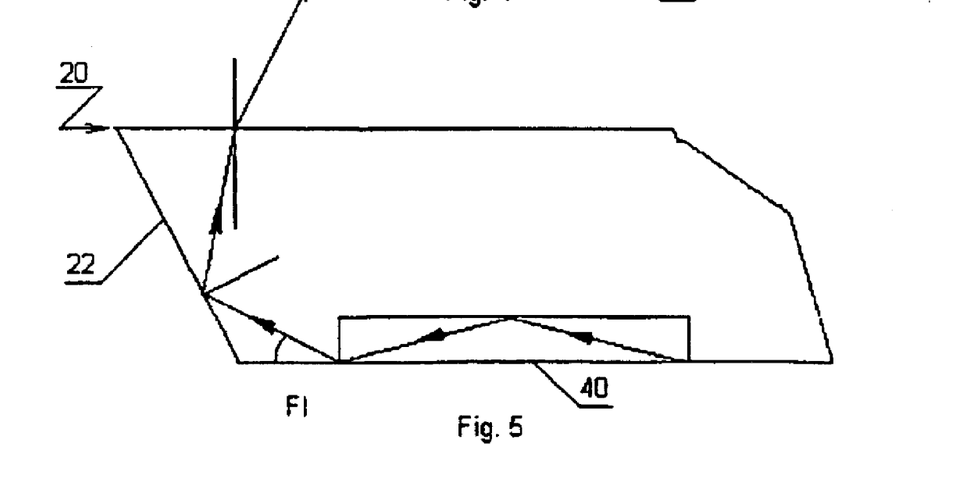
FIG. 5 is a view similar to FIGS. 3 and 4 showing further light ray patterns in a beam converger in accordance with the invention.

The reverse taper extractor 22 is shown in FIGS. 3, 4 and 5. Although these figures are shown as having trapezoidal shape, it should be realized that for the sake of clarity of explanation, the reverse extractor has a truncated conical shape and what is shown in the figures is a elevational section of the cone showing the orientation of the rays.

To understand the effect of the invention, consider an edge ray AL as shown in FIG. 3. From practical considerations, edge ray values above 72° belong to grazing rays, for which reflection losses on the die/intermediate layer boundary are very high. If the numerical aperture (sine of the acceptance half angle) of the light guide which is coupled to the converger is n, then the maximum value of BT (see FIG. 3) is:

$$BT < \arc \sin(n)$$

Figure 6:
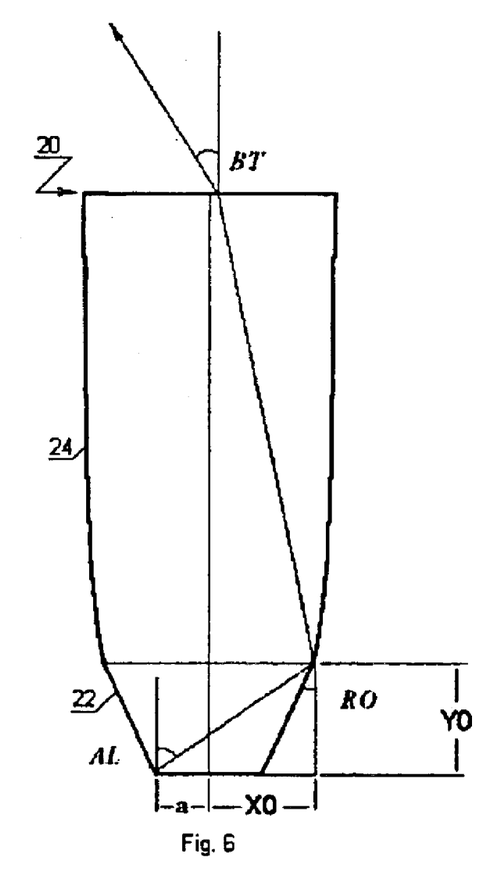
FIG. 6 is a cross-sectional view showing light ray patterns in a beam converger in accordance with the invention.

If the refraction index of the converger material is $n_2$, then the angle of the extractor portion 22 of the beam converger 20 as shown in FIG. 6, would satisfy the following condition:

$$RO = \frac{\left(AL - \arcsin\left(\frac{n}{n_2}\right)\right)}{2} \quad (5)$$

This assures that for every edge ray entering the beam converger 20 through the entrance aperture, the exit ray angle value will be equal to or less than arcsin(n). Values X0 and Y0 (see FIG. 6) for the conical section are:

$$YO = \frac{2a}{(\tan(AL) - \tan(RO))} \quad (6)$$

and $$X0 = Y0 \times \tan(RO) + a \quad (7)$$

where 2a is the entrance diameter of the taper.

The taper could enclose the die assembly as shown in FIGS. 4 and 5. This embodiment will improve the extraction efficiency allowing the rays exiting through the die side walls with angular divergence Fi greater than $$\arcsin\left(\frac{1}{n_2}\right) - RO$$

to escape through the extractor exit aperture.

This reverse taper extractor increases by as much as two times the amount of forward exit rays as compared to the bare die without the reverse taper extractor.

Figure 7:
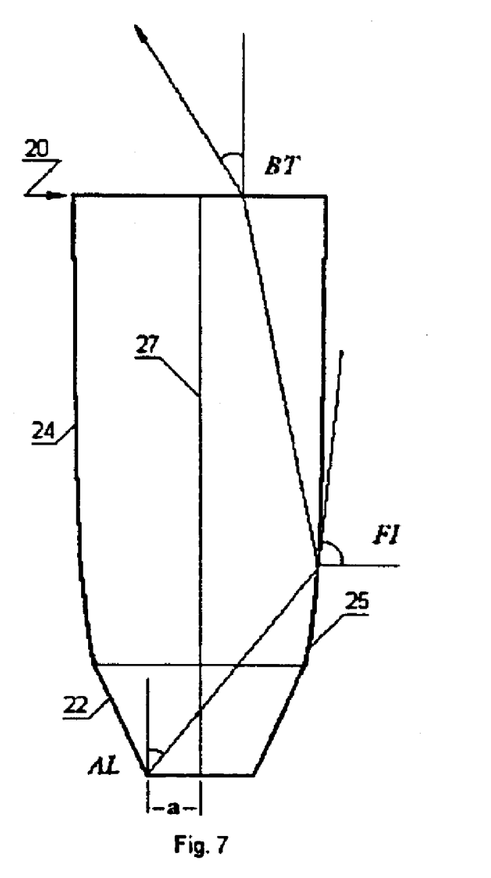
FIG. 7 is a view similar to FIG. 6 illustrating further light ray patterns in a beam converger in accordance with the invention.
Figure 9:
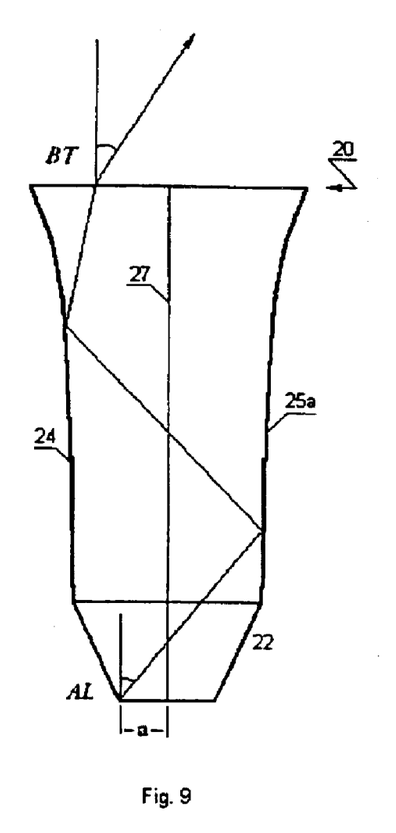
FIG. 9 is a view similar to FIG. 7 illustrating an alternate shape for a beam converger in accordance with the invention.

A beam converger 20, can be made more efficient as shown in FIGS. 6, 7 and 9, by including a collimator portion 24. The collimator portion 24 as shown in section in FIGS. 6, 7 and 9 is a rotational shape built on a circular inlet having a base 2xXO. The shape of the collimator is formed by rotating a concave, 25 (FIG. 7) or convex, 25a (FIG. 9) curve about an axis 27. This curve has a polynomial equation or put another way, has an order higher or less than 1. In the case of the curve 25 shown in FIG. 7, the tangent to the curve approaches but does not become, parallel to the axis 27 at any point. In the case of the curve 25a shown in FIG. 9, the tangent to the curve may approach but does not become perpendicular to the axis 27. For the preferred curve 25, the light ray may reflect once from the surface and then exit the collimator. In the case of the less preferred curve 25a, the light will exit the collimator 24 after multiple reflections from the collimator surface. The curves 25 and 25a which describe the edge shape of the section have a shape which preferably satisfies the following condition: a ray with an angular divergence AL emitted by the farthest point of the entrance aperture diameter of the beam extractor exits the exit aperture of the beam converger with an angular divergence less than or equal to $$BT = \arcsin(n)$$

after single or multiple reflections from the curve.

An example of the collimator part of the converger is shown in FIGS. 7 and 9. The edge curve of the cross-section as shown in FIG. 7 must satisfy the following equation:

$$Fi = \frac{dY}{dX} = \tan\frac{\left(\left(\pi + \arcsin\left(\frac{n}{n_2}\right)\right) - AL\right)}{2} \quad (8)$$

where Fi is the angle of a tangent to the curvature. This equation may be rewritten to eliminate the term AL:

$$\frac{dY}{dX} = \frac{\frac{\sin(C)xY}{\sqrt{Y^2 + (a+X)^2}} - \cos(C)x\frac{a+X}{\sqrt{Y^2 + (a+X)^2}}}{1 + \frac{\cos(C)xY}{\sqrt{Y^2 + (a+X)^2}} + \sin(C)x\frac{(a+X)}{\sqrt{Y^2 + (a+X)^2}}}$$

where $$C = \pi + \arcsin\left(\frac{n}{n_2}\right)$$

From this relationship, it will be apparent that any but the edge ray striking the curve will exit the beam converger with the angular divergence lower than arcsin(n). This beam converger is designed in such a manner that it transfers almost all of the light from its entrance aperture to its exit aperture, with the maximum angle of the exiting rays being equal to or less than the acceptance angle of a given light guide.

Figure 8:
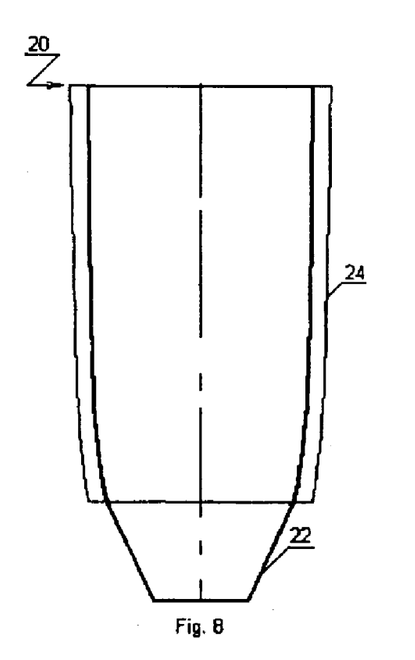
FIG. 8 is a cross-sectional view of a beam converger in accordance with an alternate embodiment of the invention.

In accordance with one aspect of the invention, the beam converger which provides the efficiencies desired, includes a combination of a solid encapsulating reverse taper extractor and a hollow beam collimator. This is shown in FIG. 8. The exit angle for this combination is equal to arcsin(n). Another alternative is to provide a solid encapsulating reverse taper extractor with a solid beam collimator. This is referred to as a solid encapsulating beam converger having an exit angle equal to arcsin(n).

Using the explanation set out above, it is possible to match the design of an extractor alone or an extractor together with a collimator to provide the requirements of the numerical aperture of the light guide with which the device is to be used.

With the above theoretical description in mind, a preferred embodiment is illustrated and discussed below.

Figure 10:
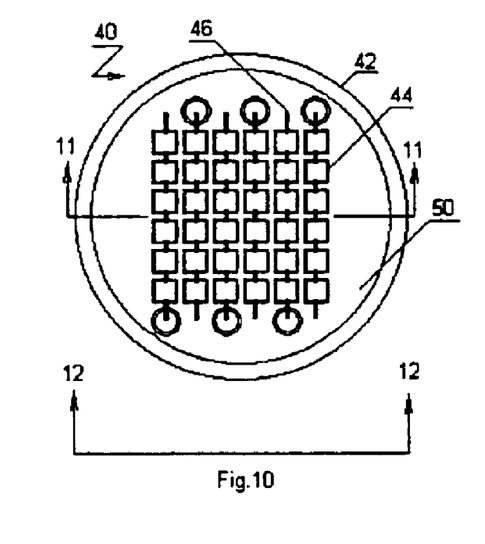
FIG. 10 is a plan view of a light source in accordance with another aspect of the invention.
Figure 11:
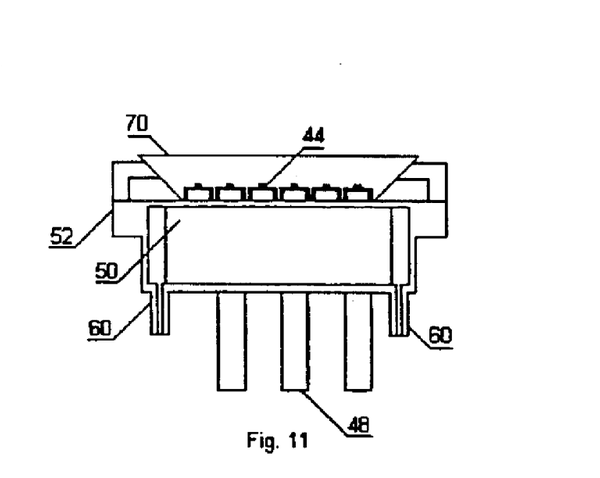
FIG. 11 is a cross-sectional view along the line 11—11 of FIG. 9.
Figure 12:
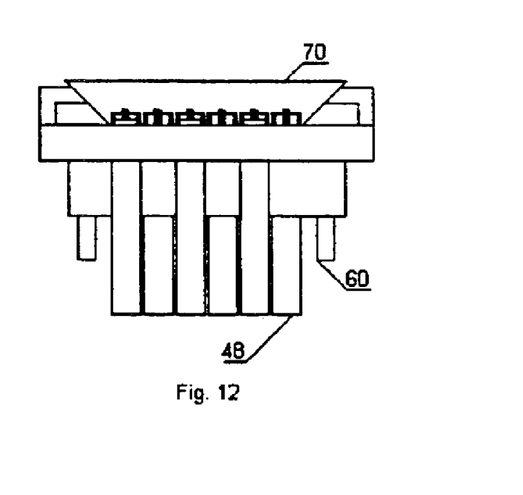
FIG. 12 is a view in the direction of the arrow 12—12 illustrated in FIG. 9.

FIG. 10 illustrates a light source indicated generally at 40. The light source 40 is illustrated in FIG. 10 in plan view. The light source 40 is contained within a cover 42. The light source 40 comprises a plurality of LED dies 44 which are conveniently arranged in a 6×6 grid as illustrated in FIG. 10. The LED dies may be LUXEON led dies from Lumiled lighting As shown in FIG. 9, each LED die in the row from the top of the page to the bottom of the page is connected to its neighbour. One end member in each row is connected to a bonding wire 46 which is connected to the case 50. Each row has a terminal pin 48 on the other end. The terminal pins may be staggered from end to end on adjacent rows to give better spacing. The terminal pins of the LUXEON LED dies are on the face side as shown in FIG. 10. The plurality of LED dies 44 are placed in contact with a heat exchanger 50 or case 52, the top surface of which is illustrated in FIG. 10. FIGS. 11 and 12 are cross-sections of the light source of FIG. 10 as illustrated in FIG. 10.

With reference to FIG. 11, it will be noted that, the terminal pins 48 for each row of LED dies, extend below the heat exchanger case 52 where they may be connected to a suitable source of electrical energy. The light source 40 illustrated in FIGS. 10, 11 and 12 is sealed by a combination of an encapsulation beam converger 70 and the cover 42.

From reference to FIG. 11, it will be noted that the light source 40 includes a relatively large heat exchanger 50. The heat exchanger 50 preferably includes a material having micro channels or suitable porosity to permit the supply of a cooling fluid through ports 60. These types of heat exchangers can provide thermal resistance of less than 0.5° C./watt. Cooling fluid may be supplied to one of the ports 60 and removed from the other port 60 after passing through the porosity or channeling within the heat exchanger 50. Heat generated by the plurality of LED dies 44 is first absorbed by the heat exchanger case 50, the heat is then passed to the heat exchanger body where the heat is released to the cooling fluid passing through the channels.

There is a relatively high thermal load. A matrix, such as shown, having 36 LUXEON LED dies might be expected to need to dissipate approximately 42 watts of heat. Thus, the heat exchanger 50 should possess a very low value of thermal resistance so as to prevent LED die overheating and consequent thermal breakdown. The cooling circuits described above are provided with sufficient capacity to meet the cooling needs of the particular LED die array selected.

Figure 13:
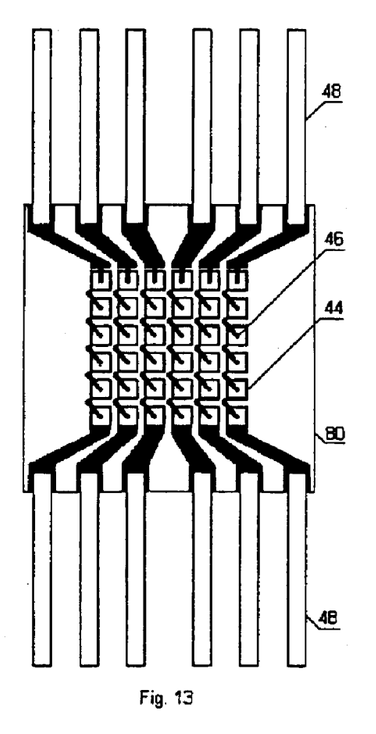
FIG. 13 is a plan view from above of the light source in accordance with another aspect of the invention.
Figure 14A:
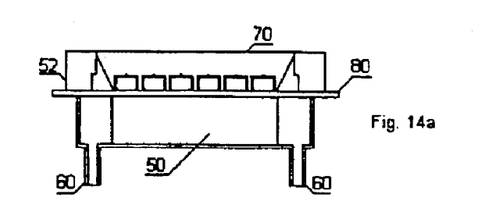
FIG. 14a is a vertical section view of an assembly including the light source of FIG. 13.
Figure 14B:
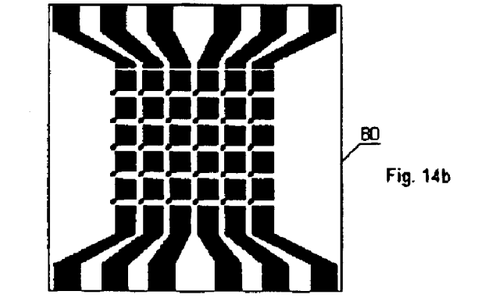
FIG. 14b is a plan view from the bottom of the light source of FIG. 13.
Figure 14C:
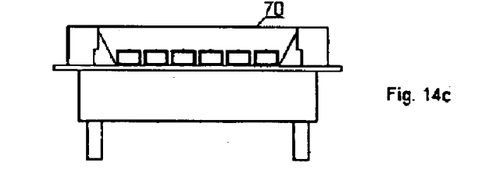

FIGS. 13 and 14 illustrate an alternate light source comprised of a heat conductive ceramic substrate 80 made, preferably, from beryllium oxide with a metalization pattern deposited on it. The LED dies 44 shown in these figures may be CREE XBRIGHT C470-XB900™. These LED dies have terminal pins located on the opposite side of the die as shown in these Figures. In this case, the terminal pins 48 are brazed to the metalization. The LED dies 44, with terminals on opposite sides of the die, are bonded to the metalization by a eutectic alloy or conductive epoxy compound and are joined in series by the bonding wire 46. In this embodiment, the heat exchanger case 82 also has micro channels or porous passageways through a heat exchanger body 84 and in and out ports 60 for coolant circulation. The heat exchanger 82 is preferably bonded to the underside of the ceramic substrate 80. In this example, the dies are sealed by an encapsulating/beam converger combination shown generally at 90 and a cover 92.

Figure 15:
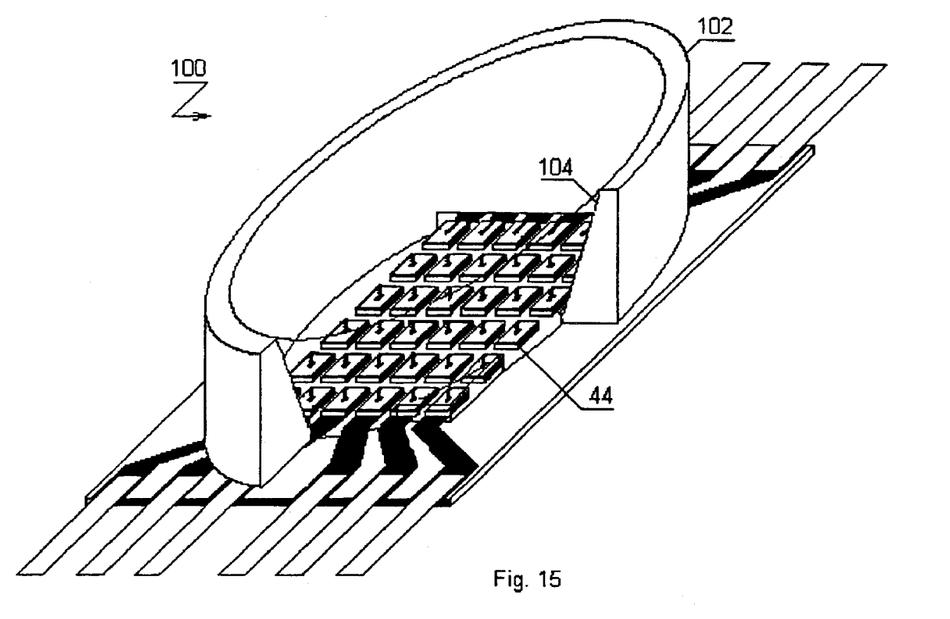
FIG. 15 is a cut away perspective view of an alternate embodiment of a light source in accordance with the invention.

FIG. 15 illustrates a light source 100 in accordance with the invention in which a reverse taper extractor is an integral part of an LED die array. In this embodiment, the component which serves as a cover 102 is comparable to cover 42 illustrated in the embodiment shown in FIGS. 10, 11 and 12 serves as a mold into which an epoxy or acrylic resin can be poured so as to encapsulate the dies and simultaneously form the reverse taper extractor. As shown in FIG. 15, the cover 102 has an interior wall 104 which slopes forwardly and outwardly away from the plane containing the plurality of LED dies 44. Advantageously, the internal walls of this mold-like structure are mirrorized or the mold itself may be made from a transparent material with an index of refraction equal to or less than 1.3. This prevents rays of light escaping from the side walls of the reverse taper extractor into the mold 102.

Figure 16:
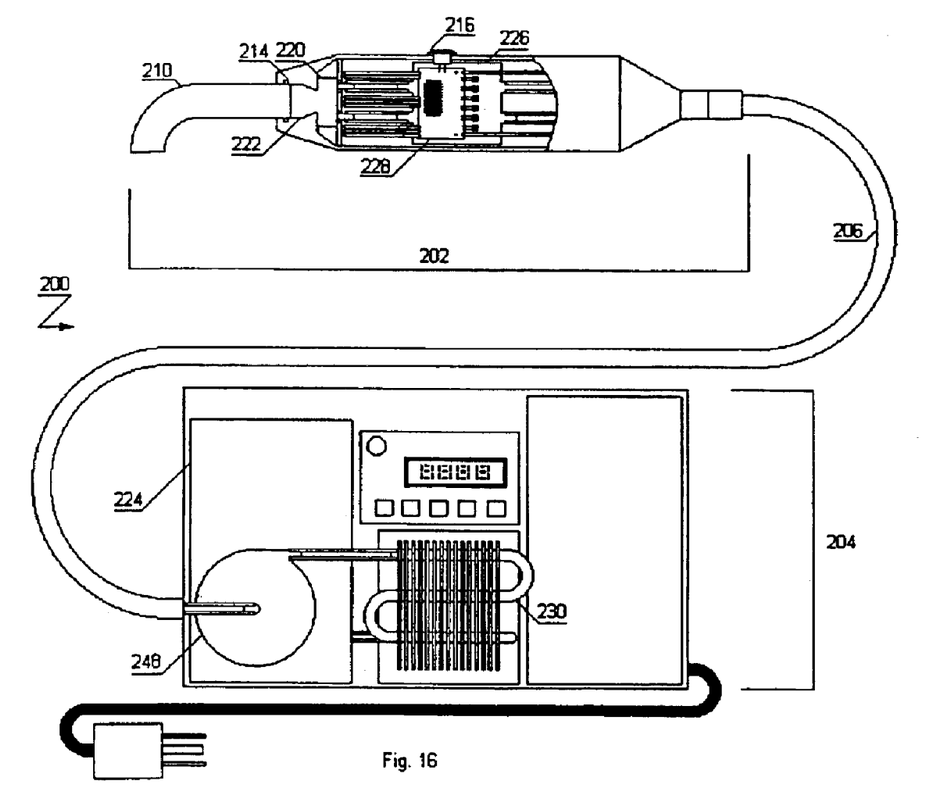
FIG. 16 is a schematic illustration in part section of a dental curing light in accordance with the invention.
Figure 17:
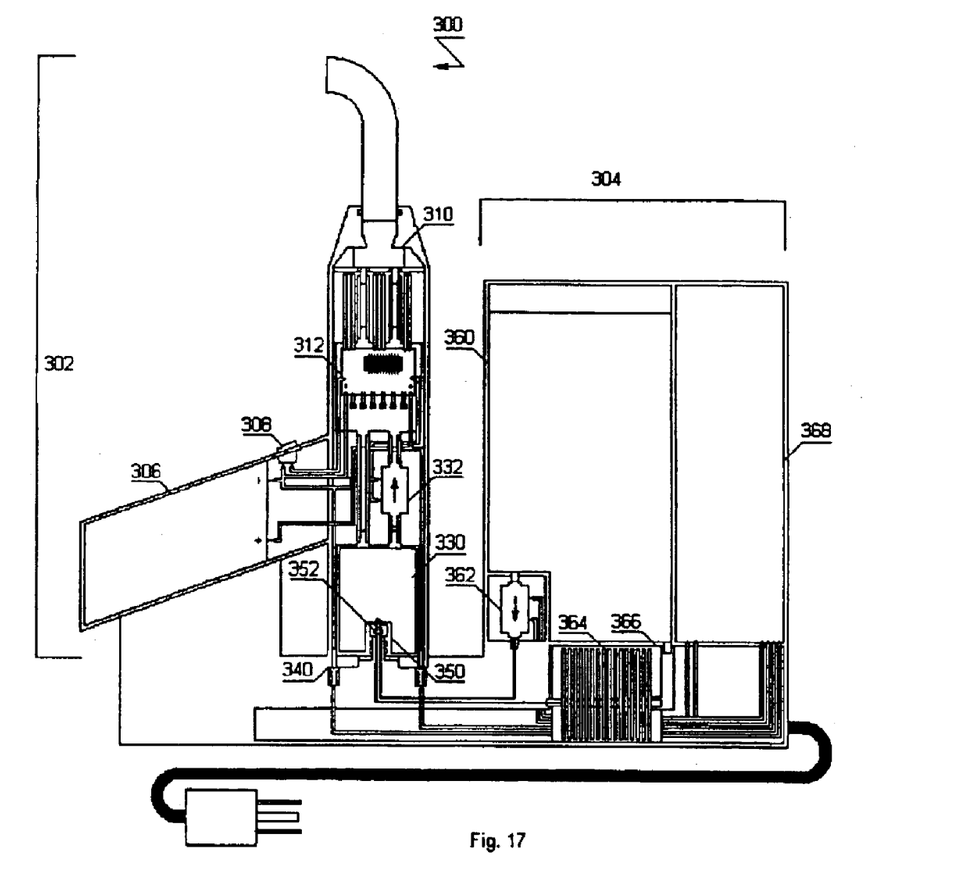
FIG. 17 is a schematic view in part section of an alternate embodiment of a dental curing light in accordance with the invention.

FIGS. 16 and 17 illustrate schematically a curing light containing a light source as discussed above. In the case of FIG. 16, there is a supply conduit connecting a base station and a hand held unit. In FIG. 17, the curing light includes a hand held unit which is detachable from and usable when disconnected from a base station.

With reference to FIG. 16, the curing light illustrated generally at 200 includes a hand held unit 202, a base station 204, and a supply conduit 206 interconnecting the hand held unit 202 and the base station 204.

The hand held unit includes a light guide 210. The light guide is maintained assembled to the hand held unit 202 by means of an O-ring 214. Various other means of affixing the light guide to the hand held unit may be used. The hand held unit includes a switch 216, for selectively energizing a light source 220, the light source 220 which is contained within the hand held unit 202, is substantially as described above. The light source 220 includes a beam converger 222, the O-ring 214 holds the inlet end of the light guide 210, closely adjacent to the outlet and in alignment with the beam converger.

The light source 220 further includes a heat sink. As discussed above, the hand held unit advantageously, includes heat conducting means, so that heat may be conducted from the heat sink of the light source. The heat sink advantageously includes channels or pores as explained above for the purpose of receiving and passing a cooling fluid through the heat sink. Where a liquid cooled heat sink is required because of the thermal output of the light source, the hand held unit 202 would then include cooling conduits for ducting cooling fluid into and out of the heat sink. Curing light 200 advantageously includes, an auxiliary heat exchanger 226 for collecting heat from power regulating components on a printed circuit board 228.

The base station 204 will include a pump 248 for moving cooling fluid from the base station 204 to the hand held unit 202. Cooling fluid is then moved from the base station 204 as needed through the supply conduit 206 to the heat sink of the light source 220 and the auxiliary heat exchanger 226.

Advantageously, the hand held unit 202 may also include a printed circuit board 228 suitable for supplying power to the light source 220. Alternatively, the printed circuit board 228 and any desirable controller features may be included in the base station 204. Electrical current including control signals and the like are then passed from the base station 204 through the supply conduit 206 to the hand held unit 202.

The base station 204 advantageously includes a heat exchanger 230 for cooling the fluid and returning it to the reservoir 224 located within the base station 204. Such cooling may be achieved by a fan moving ambient air over the heat exchanger. Alternatively, if the base station is connected directly to a dental unit, then if the dental unit has a source of cooling water, the heat exchanger, pump and second reservoir may be deleted. The controller whether located in the base station or in the hand held unit, can provide suitable power for the LEDs as well as providing various other control functions which may be useful such as count down, count up and the like. Additionally, if the controller is contained in the base station, then the controller may include a sensor so that the output from the light guide 210 can be checked from time to time to verify that the light output meets expected parameters.

Attention is now directed to FIG. 17 which illustrates a curing light shown generally as 300. In this case the curing light 300 includes a hand held unit 302 and a base station 304. The hand held unit 302 is dockable in the base station 304 and detachable from the base station 304. This curing light 300 thus permits the hand held unit to be utilized to produce the desired light when disconnected from the base station.

In this embodiment, the hand held unit 302 includes an onboard battery 306 which acts to provide a source of power for the hand held unit 302 when disconnected from the base station 304. The hand held unit 302 includes a trigger 308 for operating the light source 310 which is included within the hand held unit 302. The light source 310 is essentially similar to the light source as described above. In this case, the independent hand held unit 302 advantageously includes a controller 312 PCB for providing the necessary power supply to the light source 310 and for including the desirable control features.

Because the hand held unit 302 is not connected to the base station 304 during periods of use, and if suitably powerful LED arrays are to be used, it is likely that the hand held unit 302 will likely require a liquid cooling capacity even while removed from the base station 304. For this purpose, the hand held unit 302 includes an on board first cooling fluid reservoir 330 and a pump 332 for moving cooling fluid between the first reservoir 330 and the heat sink of the light source 310. With this structure, if the hand held unit 302 has a reservoir of approximately 100 ml, that amount of water would provide approximately one and a half minutes of working time of the light source 310 with a water temperature rise of approximately 10° C. over ambient. One and a half minutes of operation time is almost three times the amount usually required for typical, uninterrupted, clinical use, considering the amount of light output that is provided by the hand held unit 302 having the LED light source and beam converger as discussed above. As discussed above, advantageously, a six by six array of Lumiled LEDs may be used as part of the light source. An array having 36 LEDs will produce approximately 42 watts of heat, which must be dissipated. The 100 ml size of first reservoir will provide approximately one and a half minutes of run time with the temperature rise indicated above.

After the hand held unit 302 has been operated for up to one and a half minutes, it is then docked in the base station 304. While docked in the base stations 304, if the on board battery 306 requires charging, then the battery may be recharged. To accomplish that, the hand held unit includes electrical contacts 340 for connecting the battery of the hand held unit 302 to a source of charging current which will be developed by a battery charger within the base station 304.

In order to provide a fresh supply of cooling fluid to the hand held unit during the docked time period, the first reservoir of the hand held unit 302 includes fluid connection inlet ports 330 for conducting fluid into and out of the first reservoir 330. The fluid connection inlet ports 350 contain valves 352 which are in a closed position when the hand held unit 302 is removed from the base station 304. When in the closed position the valves 352 maintain the fluid within the first reservoir 330. When docked in the base station 304, however, the valves 352 are opened by the base station structure to permit the flow of fluid from the base station 304. For this purposes, the base station includes a second reservoir 360 which may be substantially larger than the first reservoir 330. The base station 304 also includes a second pump 362. Operation of the second pump 362 delivers cooled fluid from the second reservoir 360 to replace the heated fluid from the first reservoir 330. The heated fluid from the first reservoir 330 flows into the second reservoir 360. If there is a much larger amount of fluid in the second reservoir 360, the temperature rise in the second reservoir will be correspondingly smaller. After a time period sufficient to remove the warmed fluid from the first reservoir 330 and to recharge the battery 306 as necessary, the hand held unit 302 may be disconnected from the base station 304 and used for another one and a half minute period.

The base station 304 advantageously includes either a self contained heat exchanger 364 and fan 366 or is connectable to a dental unit or other source of cooling fluid so that the temperature of the second reservoir may be controlled as desired. The base station 304 may also include suitable electrical components 368 for providing the necessary charging current to the battery 306 of the hand held unit 302.

When using a dental curing light in accordance with the embodiments of the invention disclosed herein, a dentist will normally perform one or more dental procedures on a patient. Typically, these dental procedures involve using the curing light to cure a resin. Typically, the resin is first placed by the dentist where desired on a tooth and then the curing light is used to irradiate that resin and cause it to cure. There may be several applications of the light to cure resin applied to one or more teeth of a patient. However, each curing cycle typically lasts for only several seconds. In the vast majority of cases, the total time that the light is operated for any one patient will be about one minute, more or less. After the dentist has completed the curing procedures, the light would then not be used again until a subsequent patient is treated. This gives a much longer period of time to move the stored up heat that may be generated during use of the curing light.

As stated above, one preferred array is a 6 by 6 array of LUMILED LED dies. This array of 36 dies will produce approximately 42 watts of heat energy. Another desirable array might be a 5 by 5 array of the XBRIGHT C470-XB900 LEDs from Cree. This array of 25 LEDs would require dissipation of approximately 30 watts of heat energy, thus slightly reducing the amount of heat to be dissipated.

Figure 18:
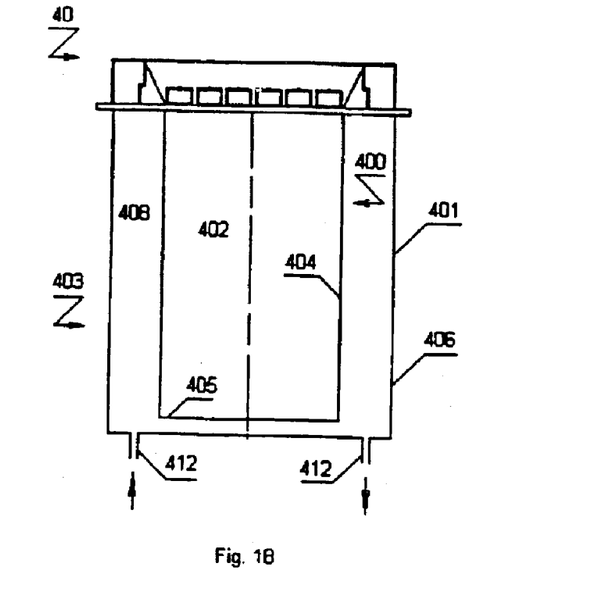
FIG. 18 is a cross section through a light source similar to FIG. 10 but embodying an alternate cooling system.

While the curing lights discussed above use water to dissipate the heat, alternate forms of heat dissipation may be embodied. FIG. 18 illustrates an alternate cooling system making use of a heat pipe. Heat pipes are available from suppliers such as AVC Asia Vital Components Limited. The heat pipe is a structure which is intended to have a relatively low heat resistance so that it can conduct heat away from a heat source relatively quickly. For example, a water filled heat pipe with a 9 mm outside diameter, may have a heat resistance of less than 0.3 watt per degree Celcius under a heat load of 100 watts. The heat pipe thus provides an efficient alternative for conducting heat away from a light source consisting of LED dies. The heat pipe is placed adjacent to the case or heat sink in which the LED dies are mounted so as to provide efficient transfer of heat from the LEDs dies directly to one end of the heat pipe.

Figure 19:
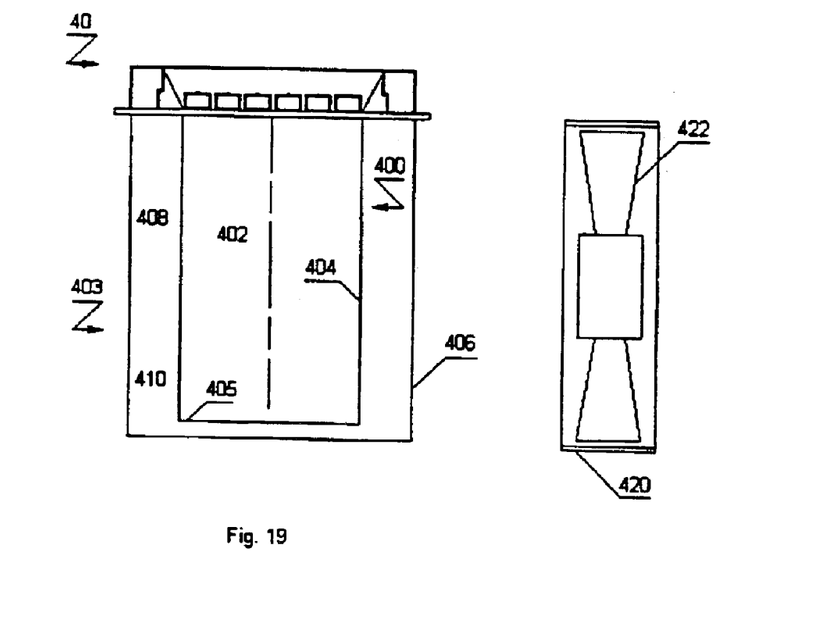
FIG. 19 is a view similar to FIG. 18 illustrating a light source including a further alternative cooling system

In FIG. 19, a light source 40 is shown connected to a heat dissipating assembly 403 which includes a heat pipe 400 and a cooling jacket 401. The heat pipe 400 has an internal chamber 402 which is bounded by a cylindrical wall 404 and an end wall 405. The chamber 402 can be filled with water and with other structures which helps conduct the heat away from the end of the heat pipe which is adjacent to the light source 40. The cooling jacket 401 includes an outer wall 406. There is created an annular space or chamber 408 about the inner wall 404 which surrounds the heat pipe over its length. The chamber 408 may extend across the end wall 405 of the heat pipe which is remote from the light source 40. The cooling jacket 401 may further include coolant ports 412 for conducting a cooling fluid into and out of the chamber 408.

In operation, the heat generated by the light source 40 is conveyed away from the light source 40 by the heat pipe 400. The quantity of heat is first passed to the liquid within the chamber 402. The liquid evaporates into the space within the chamber 402 and hot steam consequently transfers heat to the cylindrical wall 404 and end wall 405 which ultimately transfers heat into the liquid within the chamber 408. The liquid within the chamber 408 may be water which is supplied through the ports 412. The ports 412 may be supplied from a pump and reservoir such as that illustrated in the base unit 204 as illustrated in FIG. 16.

If it is desired to make use of the heat pipe technology in connection with a hand held unit which is separable from a base station, that may be accomplished using the structure illustrated in FIG. 19. FIG. 19 illustrates a heat dissipating assembly 403 which includes a heat pipe 400 and a cooling jacket 401 which is attached to a light source 40. In this case, the heat pipe 400 has an internal chamber 402 formed by an internal cylindrical wall 404 and an end wall 405. The cooling jacket 401 has an outer wall 406. There is a chamber 408 created between the inner wall 404 and the outer wall 406. In this case, the chamber 408 is an annular space extending the length of the heat pipe and may have a space at the end of the heat pipe remote from the light source 40.

In this particular heat dissipating assembly 403, the chamber 408 is filled with a cooling medium 410. The cooling medium 410 includes a media which changes phase at an acceptable temperature, typically between 40° C. and 60° C. Useful materials include the alloy sold under the trade mark OSTALLOY 117™, the alloy UM47™ sold by Umicore Electro-Optic Materials, or less desirably organic products known under the trade mark ClimSell C48™ from Clymator AB. The first two of these products are solid metal at room temperature and have very good thermal conductivity. The ClimSell product is an organic solid which does not have as high conductivity. All of these products, however, change from a solid to a liquid at approximately 47 to 48° C. All three of these materials have very high latent heat of fusion and thus are able to "absorb" fairly large amounts of heat without changing temperature. By way of example, the latent heat of fusion of OSTALLOY 117 is 36.8 J/gm. The latent heat of fusion for ClimSell C48 is much higher, approximately 216 J/gm. However, because the conductivity of OSTALLOY 117 is higher, it is the preferred phase change media, notwithstanding its lower latent heat of fusion. For example, 100 gms of OSTALLOY 117 would "absorb" 3,680 J at the phase change temperature.

This amount of heat is more than sufficient to ensure uninterrupted use of a curing light composed of 25 dies from Cree as discussed above, which might be expected to require dissipation of approximately 30 watts of heat. By providing over two minutes of working time, this is more than sufficient for a dentist to deal with one patient.

The heat dissipative assembly 403 illustrated in FIG. 19 would be accommodated within the hand held unit 302 illustrated in FIG. 17 and would eliminate the need for an internal reservoir, pump and water cooled heat exchanger. The dissipative assembly 403 would be located in the hand held unit 302, firstly, so that it would have sufficient heat dissipation directly from the light source 310, but, also would be available to be received within a receptacle 420 which may be contained within the base unit 304. The receptacle 420 would be sized to accommodate the outer wall 406. The receptacle can then be equipped with a fan 422 which can be used to drive ambient air over the outer surface of the wall 406 to remove the heat from the heat dissipative assembly 403. In this sense, the heat dissipative assembly 403 not only conducts heat, but by use of the phase change liquid, serves as a storage module for heat. Given that the normal time between patients would probably exceed 15 minutes, there would be more than ample time between patients for the dental professional to obtain full cooling of the heat pipe down to ambient temperature. If more rapid cooling was required, the receptacle 420 could be liquid cooled by circulation of cooling fluid from the dental unit rather than using a fan and ambient air for cooling.

The curing light source as discussed above, is capable of producing high power light output of over 2,000 mW/sq cm. This makes the light suitable for cure times which are comparable with other types of lighting commercially available while providing the advantages of the LED's desirable light spectrum out puts. If there are circumstances in which a lower level of light output is required, then the beam converger as described above, remains significantly advantageous. If fewer LEDs of this size are involved in the array, the heat to be removed may be lessened to the point that instead of using liquid cooling or heat pipe cooling as described in more detail herein, it may be possible to use a fan to blow ambient air across the heat sink or to heat pipes connected with the heat sink and to provide sufficient cooling. Thus, the advantages of the light source disclosed herein are applicable to both high powered and lower powered curing lights.

While LEDs commercially available today would most likely be used in an array as discussed herein, the invention is not limited to an array or an array of any particular number or configuration. When single LEDs of larger size and power become economically available, a single LED may be used in place of a plurality of LEDs in an array.

Further and other changes may be made to the invention without departing from the scope of the invention, the above description is considered to be illustrative only and the full scope of the invention is set out in the following claims.

What is claimed is:

1. A light source for a curing light,
    said light source comprising at least one LED die;
    electrical connection means for conducting electric current to energize said LED die,
    said LED die arranged with a light emitting face arranged to emit light in the forward direction relative to said LED die,
    a beam converger adjacent said light emitting face,
    said beam converger including an extractor portion, said extractor portion having a truncated generally conical shape which tapers outwardly and forwardly relative to said LED die.

2. The light source of claim 1 wherein said light source comprises a plurality of LED dies and said LED dies are arranged in an array with light emitting faces arranged to emit light in said forward direction.

3. The light source of claim 2, wherein
    said beam converger includes a collimator portion adjacent the extractor portion and said collimator portion has a surface shape formed by rotating a concave curve about an axis extending away from said extractor portion, and the tangent to that curve at any point approaches but does not become parallel to the axis of rotation above the extractor.

4. The light source of claim 2 wherein,
    said beam converger includes a collimator portion adjacent the extractor portion and said collimator portion has a surface shape formed by rotating a convex curve about an axis extending away from said extractor portion, and the tangent to that curve at any point does not become perpendicular to the axis.

5. The light source of claim 3 wherein said collimator is solid and said surface is the exterior surface.

6. The light source of claim 3 wherein said collimator is hollow and said surface is a mirrored internal surface for reflecting light.

7. The light source of claim 3, wherein said extractor portion encapsulates said array of LED dies.

8. In combination, the light source of claim 3 and a light guide, said light guide having an acceptance angle wherein the maximum angle of light rays exiting said beam converger is equal to or less than said acceptance angle of said light guide.

9. The combination of claim 8 wherein said beam converger includes a collimator portion having a maximum exit angle equal to arc sine (n) where n is the numerical aperture of the light guide.

10. The light source of claim 3 wherein the light source includes a heat sink for conducting heat away from the array of LED dies.

11. A curing light comprising
a hand held unit and a base station, the hand held unit including the light source of claim 10,
said curing light including a power supply for supplying electrical energy to the light source, and
a controller for controlling electrical flow to the LED dies, and further including
a source of cooling fluid, and
circulation means for circulating cooling fluid to the heat sink.

12. The light source of claim 10 wherein said heat sink includes passageways for conducting fluid through said heat sink.

13. The light source of claim 12 wherein said passageways are micro channels.

14. The curing light of claim 11 wherein,
said power source includes a battery contained within said hand held unit,
and wherein,
said hand held unit includes a first cooling fluid reservoir and a first pump for circulating fluid from the first reservoir to the heat sink.

15. The curing light of claim 14 wherein the hand held unit includes electrical connection means for receiving an electrical current from said base station to recharge said battery.

16. The curing light of claim 14 wherein the base station includes a second cooling fluid reservoir and said hand held unit includes fluid connection inlet ports for conducting fluid into and out of the first cooling reservoir from the second cooling reservoir.

17. The curing light of claim 16 wherein the hand held unit and the base station are separate from each other.

18. The curing light of claim 17 wherein the hand held unit inlet ports include valves and said base station includes receiving ports for connecting with the inlet ports of the hand held unit and for opening the valves and the hand held unit is connectable with and disconnectable from the base station so that the hand held unit may be used to produce light when disconnected from the base station.

19. The curing light of claim 11 wherein the curing light includes a supply conduit for conducting cooling fluid between the base station and the hand held unit.

20. The curing light of claim 11 wherein the curing light includes a heat dissipating assembly and the heat dissipating assembly includes a heat pipe located adjacent said heat sink.

21. The curing light of claim 20 wherein the heat dissipating assembly further includes a cooling jacket for transferring heat from said heat pipe.

22. The curing light of claim 21 wherein the cooling jacket of said heat dissipating assembly contains a phase change material which changes from a solid to a liquid at a temperature of from 40° C. to 60° C. and said phase change material has a latent heat of fusion of at least 30 J/gm.

23. The curing light of claim 21 wherein the cooling fluid is water and the water is circulated through the cooling jacket.

24. In combination, a light source for a curing light,
said light source comprising at least one LED die;
electrical connection means for conducting electric current to energize said LED die,
said LED die arranged with a light emitting face arranged to emit light in the forward direction relative to said LED die,
a beam converger adjacent said light emitting face,
said beam converger including an extractor portion, said extractor portion having a truncated generally conical shape which tapers outwardly and forwardly relative to said LED die,
and wherein said light source comprises a plurality of LED dies and said LED dies are arranged in an array with light emitting faces arranged to emit light in said forward direction, and wherein
said beam converger includes a collimator portion adjacent the extractor portion and said collimator portion has a surface shape formed by rotating a concave curve about an axis extending away from said extractor portion, and the tangent to that curve at any point approaches but does not become parallel to the axis of rotation above the extractor and a light guide, said light guide having an acceptance angle wherein the maximum angle of light rays exiting said beam converger is equal to or less than said acceptance angle of said light guide,
and wherein said beam converger includes a collimator portion having a maximum exit angle equal to arc sine (n) where n is the numerical aperture of the light guide.

25. A light source for a curing light,
said light source comprising at least one LED die;
electrical connection means for conducting electric current to energize said LED die,
said LED die arranged with a light emitting face arranged to emit light in the forward direction relative to said LED die,
a beam converger adjacent said light emitting face,
said beam converger including an extractor portion, said extractor portion having a truncated generally conical shape which tapers outwardly and forwardly relative to said LED die, and wherein
said light source comprises a plurality of LED dies and said LED dies are arranged in an array with light emitting faces arranged to emit light in said forward direction, and wherein
said beam converger includes a collimator portion adjacent the extractor portion and said collimator portion has a surface shape formed by rotating a concave curve about an axis extending away from said extractor portion, and the tangent to that curve at any point approaches but does not become parallel to the axis of rotation above the extractor, and wherein
the light source includes a heat sink for conducting heat away from the array of LED dies, and wherein
said heat sink includes passageways for conducting fluid through said heat sink, and wherein
said passageways are micro channels.

26. The light source of claim 25 wherein said passageways comprise porosity of said heat sink.

27. A light source for a curing light,
said light source comprising at least one LED die;
electrical connection means for conducting electric current to energize said LED die, said LED die arranged with a light emitting face arranged to emit light in the forward direction relative to said LED die, a beam converger adjacent said light emitting face, said beam converger including an extractor portion, said extractor portion having a truncated generally conical shape which tapers outwardly and forwardly relative to said LED die, and wherein said light source comprises a plurality of LED dies and said LED dies are arranged in an array with light emitting faces arranged to emit light in said forward direction, and wherein said beam converger includes a collimator portion adjacent the extractor portion and said collimator portion has a surface shape formed by rotating a concave curve about an axis extending away from said extractor portion, and the tangent to that curve at any point approaches but does not become parallel to the axis of rotation above the extractor, and wherein the light source includes a heat sink for conducting heat away from the array of LED dies, and wherein said heat sink includes passageways for conducting fluid through said heat sink, and wherein said passageways comprise porosity of said heat sink.

28. In combination a light source for a curing light, said light source comprising at least one LED die;

electrical connection means for conducting electric current to energize said LED die, said LED die arranged with a light emitting face arranged to emit light in the forward direction relative to said LED die, a beam converger adjacent said light emitting face, said beam converger including an extractor portion, said extractor portion having a truncated generally conical shape which tapers outwardly and forwardly relative to said LED die and a light guide, said light guide having an acceptance angle wherein the maximum angle of light rays exiting said beam converge is equal to or less than said acceptance angle of said light guide, and wherein said beam converger includes a collimator portion having a maximum exit angle equal to arc sine (n) where n is the numerical aperture o the light guide.

29. The light source of claim 28 wherein said light source comprises a plurality of LED dies and said LED dies are arranged in an array with light emitting faces arranged to emit light in said forward direction.

30. The light source of claim 28 wherein said beam converger includes a collimator portion adjacent the extractor portion and said collimator portion has a surface shape formed by rotating a concave curve about an axis extending away from said extractor portion, and the tangent to that curve at any point approaches but does not become parallel to the axis of rotation above the extractor.

31. The light source of claim 28 wherein, said beam converger includes a collimator portion adjacent the extractor portion and said collimator portion has a surface shape formed by rotating a convex curve about an axis extending away from said extractor portion, and the tangent to that curve at any point does not become perpendicular to the axis.

32. The light source of claim 28 wherein said collimator is solid and said surface is the exterior surface.

33. The light source of claim 28 wherein said collimator is hollow and said surface is mirrored internal surface for reflecting light.

34. The light source of claim 28 wherein the light source includes a heat sink for conducting heat away from the array of LED dies.

35. The light source of claim 28 wherein said heat sink includes passageways for conducting fluid through said heat sink.

36. The light source of claim 28 wherein said passageways are micro channels.

37. The light source of claim 28 wherein said passageways comprise porosity of said heat sink.

38. A light source for a curing light, said light source comprising at least one LED die;

electrical connection means for conducting electric current to energize said LED die, said LED die arranged with a light emitting face arranged to emit light in the forward direction relative to said LED die, a beam converger adjacent said light emitting face, said beam converger including an extractor portion, said extractor portion having a truncated generally conical shape which tapers outwardly and forwardly relative to said LED die, and wherein said extractor portion encapsulates said array of LED dies.

39. The light source of claim 38 wherein said light source comprises a plurality of LED dies and said LED dies are arranged in an array with light emitting faces arranged to emit light in said forward direction.

40. The light source of claim 38, wherein said beam converger includes a collimator portion adjacent the extractor portion and said collimator portion has a surface shape formed by rotating a concave curve about an axis extending away from said extractor portion, and the tangent to that curve at any point approaches but does not become parallel to the axis of rotation above the extractor.

41. The light source of claim 38 wherein, said beam converger includes a collimator portion adjacent the extractor portion and said collimator portion has a surface shape formed by rotating a convex curve about an axis extending away from said extractor portion, and the tangent to that curve at any point does not become perpendicular to the axis.

42. The light source of claim 38 wherein said collimator is solid and said surface is the exterior surface.

43. The light source of claim 38 wherein said collimator is hollow and said surface is a mirrored internal surface for reflecting light.

44. The light source of claim 38 wherein the light source includes a heat sink for conducting heat away from the array of LED dies.

45. The light source of claim 38 wherein said heat sink includes passageways for conducting fluid through said heat sink.

46. The light source of claim 38 wherein said passageways are micro channels.

47. The light source of claim 38 wherein said passageways comprise porosity of said heat sink.

* * * * *